United States Patent
Calton

(10) Patent No.: US 11,285,124 B2
(45) Date of Patent: Mar. 29, 2022

(54) COMPOSITIONS AND METHODS FOR INCREASING MUSCLE MASS AND STRENGTH, TREATING SKIN, REDUCING WEAR AND DEGRADATION FROM AGING AND EXPOSURE AND IMPROVING RECOVERY FROM STRESS SUCH AS EXERCISE AND TRAUMA

(71) Applicant: CALWOOD NUTRITIONALS, LLC, Sykesville, MD (US)

(72) Inventor: Gary Calton, Sykesville, MD (US)

(73) Assignee: CALWOOD NUTRITIONALS, LLC, Sykesville, MD (US)

( * ) Notice: Subject to any disclaimer, the term of this patent is extended or adjusted under 35 U.S.C. 154(b) by 75 days.

(21) Appl. No.: 16/639,233

(22) PCT Filed: Aug. 16, 2018

(86) PCT No.: PCT/US2018/000226
§ 371 (c)(1),
(2) Date: Feb. 14, 2020

(87) PCT Pub. No.: WO2019/035953
PCT Pub. Date: Feb. 21, 2019

(65) Prior Publication Data
US 2020/0215011 A1 Jul. 9, 2020

Related U.S. Application Data

(60) Provisional application No. 62/547,407, filed on Aug. 18, 2017.

(51) Int. Cl.
| | |
|---|---|
| *A61K 31/198* | (2006.01) |
| *A23L 33/175* | (2016.01) |
| *A61P 21/00* | (2006.01) |
| *A61K 9/00* | (2006.01) |
| *A61K 31/197* | (2006.01) |
| *A61K 31/405* | (2006.01) |
| *A61K 31/4172* | (2006.01) |

(52) U.S. Cl.
CPC .......... *A61K 31/198* (2013.01); *A23L 33/175* (2016.08); *A61K 9/0053* (2013.01); *A61K 31/197* (2013.01); *A61K 31/405* (2013.01); *A61K 31/4172* (2013.01); *A61P 21/00* (2018.01); *A23V 2002/00* (2013.01)

(58) Field of Classification Search
CPC .................................................... A61K 31/198
See application file for complete search history.

(56) References Cited

U.S. PATENT DOCUMENTS

| | | |
|---|---|---|
| 4,112,123 A | 9/1978 | Roberts |
| 5,026,721 A * | 6/1991 | Dudrick .............. A61K 31/195 514/396 |
| 6,077,828 A | 6/2000 | Abbruzzes et al. |
| 6,203,820 B1 | 3/2001 | Vickery |
| 6,420,342 B1 | 7/2002 | Hageman et al. |
| 6,713,501 B1 | 3/2004 | Walser |
| 8,703,725 B2 | 4/2014 | Troup et al. |
| 8,716,249 B2 | 5/2014 | Wolfe et al. |
| 9,364,463 B2 | 6/2016 | Ferrando et al. |
| 9,597,367 B2 | 3/2017 | Wolfe et al. |
| 2007/0286909 A1 | 12/2007 | Smith et al. |
| 2010/0267831 A1* | 10/2010 | Kobayashi ............... A61P 3/02 514/561 |

FOREIGN PATENT DOCUMENTS

| | | |
|---|---|---|
| GB | 2 082 911 A | 3/1982 |
| WO | 1989/004165 | 5/1989 |
| WO | 91/09524 | 7/1991 |

OTHER PUBLICATIONS

Ferrando, AA et al., "Oral Branched chain Amino Acids Decrease Whole body Proteolysis", JPEN J Parenter Enteral Nutr., 19(1), 1995, pp. 47 54.
Fouré, A et al., "Effects of branched-chain amino acids supplementation on both plasma amino acids concentration and muscle energetics changes resulting from muscle damage: A randomized placebo controlled trial", Clin Nutr., 35(1), 2016, pp. 83-94.
Fouré, A et al., "Is Branched-Chain Amino Acids Supplementation an Efficient Nutritional Strategy to Alleviate Skeletal Muscle Damage? A Systematic Review", Nutrients, 9(10), 2017, PP.
De Bandt, JP et al., "Therapeutic use of branched-chain amino acids in burn, trauma, and sepsis", J Nutr., 136(1 Suppl):, 2006, pp. 308S-313S.
Tipton, KD , "Branched-chain Amino Acid Supplementation to Support Muscle Anabolism Following Exercise", 2017, PP.
Tipton, KD et al., "Postexercise Net Protein Synthesis in Human Muscle from Orally Administered Amino Acids", Am J Physiol, 276(4 Pt 1), 1999, pp. E628 E634.
Paddon Jones, D et al., "Amino Acid Ingestion Improves Muscle Protein Synthesis in the Young and Elderly", Am J Physiol Endocrinol Metab., 286(3), 2004, pp. E321 E328.
Baldissarro, E et al., "The Hip Functional Retrieval after Elective Surgery May Be Enhanced by Supplemented Essential Amino Acids", Biomed Res Int. 2016, 2016, pp. 9318329.
Dreyer, HC et al., "Essential Amino Acid Supplementation in Patients Following Total Knee Arthroplasty", J Clin Invest., 123(11), 2013, pp. 4654 4666.

(Continued)

*Primary Examiner* — Rei Tsang Shiao
(74) *Attorney, Agent, or Firm* — Greenblum & Bernstein, P.L.C.

(57) ABSTRACT

Compositions comprising an amino acid component including: L-histidine, L-isoleucine, L-leucine, L-lysine, L-phenylalanine, L-threonine, L-tryptophan, L-valine and L-arginine and optimized levels of L-methionine. L-tryptophan content may also be elevated and optimized, and additional amino acids including arginine, L-arginine, L-citrulline, L-carnitine and L-cysteine may optionally be present. Methods of treating muscle, wounds, surgical procedures, skin conditions and other conditions using such compositions are also provided.

23 Claims, No Drawings

(56) References Cited

OTHER PUBLICATIONS

"Ncbinlmnihgov", Estimates of Amino Acid Requirements—Recommended Dietary Allowances—NCBI Bookshelf, 2017, PP.
Borsheim et al., "Amino acid supplementation decreases plasma and liver triacylglycerols in elderly", Nutrition, vol. 25, No. 3, 2009, pp. 281-288.
Official Communication issued in International Bureau of WIPO Patent Application No. PCT/US2018/000226, dated Dec. 17, 2018.
Extended European Search Report issued in European Patent Application No. 18 846 666.8 dated Mar. 12, 2021.
Bralley et al. Treatment of Chronic Fatigue Syndrome with specific Amino Acid Supplementation, Journal of Applied Nutrition, Vo. 46, No. 3 dated Jan. 1, 1994, pp. 74-78, XP055534423.
Glutamine producing prepn. For preventing mucosa atrophy, etc.—comprises L-leucine, L-isoleucine, L-valine, L-lysine, L-threonine, L-tryptophan, L-methionine, L-phenyl-alanine etc:, Derwent, 1994, XP002183128.
Aminoacid Compsn, for Fatigue Recovery—contains Essential Aminoacid Mixt, Contg. E.G. Valine, Leucine, Iosleucine, Lyisne and M: WPI World Patent Information Derwent, vol. 18, No. 97, 1997, XP002092563.

\* cited by examiner

COMPOSITIONS AND METHODS FOR INCREASING MUSCLE MASS AND STRENGTH, TREATING SKIN, REDUCING WEAR AND DEGRADATION FROM AGING AND EXPOSURE AND IMPROVING RECOVERY FROM STRESS SUCH AS EXERCISE AND TRAUMA

CROSS-REFERENCE TO RELATED APPLICATIONS

This application is a U.S. national stage of PCT/US2018/000226, filed Aug. 16, 2018, which claims the benefit of U.S. Provisional Application No. 62/547,407, filed Aug. 18, 2017. U.S. Provisional Application No. 62/547,407, filed Aug. 18, 2017 is hereby incorporated by reference in its entirety as though set forth in full herein.

BACKGROUND OF THE INVENTION

1. Field of the Invention

The present invention generally relates to compositions and methods for increasing and maintaining muscle mass, strength, and functional performance in young and old, and for improving: time for recovery from fatigue, strength recovery after exercise, soreness relief, skin tone, cosmetic reduction of wrinkles and fine lines and acne, wound healing, cancer cachexia, sarcopenia, diet after bariatric surgery, scar coloration, scar reduction, scar minimization, and scar appearance by delivering a selection of amino acids. The compositions comprise a selection of essential and, optionally, semi-essential amino acids.

2. Discussion of Background Information

Amino acids have been employed as nutritional supplements, and attempts have been made to employ amino acids in formulations in efforts to promote human and veterinary health. In general, such attempts have involved relatively large amounts of amino acids in order to achieve desired and/or meaningful beneficial results.

The number of possible potential formulations of the essential amino acids for improvement in muscle mass is vast as there are nine essential amino acids in man and additional semi-essential and conditional amino acids which may potentially add to the biological value of a nutritional formula for treatment of disease or to supply nutrition. Although the stereospecificity of the amino acids is not indicated at times in this specification, it should be understood that the L form is used in animal subjects, including humans, except where the D form has been found to be useful in animal nutrition, including humans.

Oral ingestion of branched chain amino acids (leucine, isoleucine, and valine) formulas has been shown not to affect protein synthesis and breakdown, but an equivalent amount of the essentials (threonine, methionine, and histidine) increased protein synthesis and breakdown. (*Oral Branched-chain Amino Acids Decrease Whole-body Proteolysis*, Ferrando A A, Williams B D, Stuart C A, Lane H W, Wolfe R R. JPEN J Parenter Enteral Nutr. 1995 January-February; 19(1):47-54.

Branched chain amino acids have been cited as compositions suitable for the purpose of preventing cachexia and anorexia. See for example, Abbruzzee et al., who in U.S. Pat. No. 6,077,828 for a formulation for treatment of cancer and anorexia comprising both essential and non-essential amino acids having 2.8% methionine, stated that the branched chain amino acids have bitter and sour tastes which make them "less than ideal for a ready-to-use oral nutritional composition and thus required encapsulation or pill formation" (column 15, lines 1-15).

Roberts discloses in U.S. Pat. No. 4,112,123, the use of 15-50% of BCAA in the form of whey, which has been shown to be much less effective than the free form essential amino acids and contains insufficient amounts of methionine and large quantities of nonessential amino acids which have been shown to far less effective the free essential amino acids alone (see U.S. Pat. No. 8,703,725).

Continued research has shown that BCAAs supplementation can be efficacious on outcomes of exercise-induced muscle damage, as long as the extent of muscle damage was low-to-moderate, and the supplementation strategy combined a high daily BCAAs intake (>200 mg kg-1 day-1). (*Is Branched-Chain Amino Acids Supplementation an Efficient Nutritional Strategy to Alleviate Skeletal Muscle Damage? A Systematic Review*. Fouré A, Bendahan D. Nutrients. 2017 September 21; 9(10). *Effects of branched-chain amino acids supplementation on both plasma amino acids concentration and muscle energetics changes resulting from muscle damage: A randomized placebo controlled trial*. Fouré A, Nosaka K, Gastaldi M, Mattei J P, Boudinet H, Guye M, Vilmen C, Le Fur Y, Bendahan D, Gondin J., Clin Nutr. 2016 February; 35(1):83-94 0

Additionally BCAA's have been shown to be ineffective in burns, trauma and sepsis (*Therapeutic use of branched-chain amino acids in burn, trauma, and sepsis*. De Bandt J P, Cynober L. J Nutr. 2006 January; 136(1 Suppl):308S-13S.

In a review of BCAA, Tipton points out, "There is insufficient evidence to indicate that BCAA ingestion is effective for stimulating muscle protein synthesis following endurance exercise; there is no evidence that BCAA ingestion inhibits post-exercise muscle protein breakdown in humans and it is not clear that a nutritional intervention, including BCAA ingestion, aimed at inhibiting post-exercise muscle protein breakdown is a positive goal; and the evidence for use of BCAA as a countermeasure to reduce exercise-induced muscle damage is, at best, equivocal and not as clear as touted by many sources" (*Branched-chain Amino Acid Supplementation to Support Muscle Anabolism Following Exercise*, September 2017, Kevin D. Tipton, PhD accessed at http://www.gssiweb.org/en/sports-science-exchange/Article/branched-chain-amino-acid-supplementation-to-support-muscle-anabolism-following-exercise).

Hageman, in U.S. Pat. No. 6,420,342, discloses a combination of amino acids which does not include tryptophan in the mixture, making it nutritionally incomplete, and thus incapable of promoting muscle synthesis as claimed. In the application for U.S. Pat. No. 9,364,463, related to this composition, it was stated that it was necessary to add tryptophan (0.06%) and additional valine and isoleucine before strength was improved.

Vickery, U.S. Pat. No. 6,203,820 discloses the use of molybdenum and a mixture of essential amino acids, excluding tryptophan, (Example 1) although claimed and found that the essential amino acids alone did not have an effect on the muscle or protein anabolism of the test subject (Example 3, column 8, lines 26-34; Example 5, column 9, lines 15-21)

Various approaches have been undertaken to arrive at possible optimum formulations, without consensus on an optimum approach. In other words, workers have tried approaches from various directions. Continued study of muscle protein metabolism has resulted in numerous improvements as non-essential amino acids were shown not necessary for the anabolic effect of oral amino acid mixtures where a formula having no tryptophan and only 3.8% methionine was used. (*Postexercise Net Protein Synthesis in Human Muscle from Orally Administered Amino Acids*, Tipton K D, Ferrando A A, Phillips S M, Doyle D Jr, Wolfe R R. Am J Physiol. 1999 April; 276(4 Pt 1):E628-34. The same formula (11 g/dose, 2 doses/day) showed improved muscle synthesis in the young and elderly. (*Amino Acid Ingestion Improves Muscle Protein Synthesis in the Young and Elderly*, Paddon-Jones D, Sheffield-Moore M, Zhang X J, Volpi E, Wolf S E, Aarsland A, Ferrando A A, Wolfe R R. Am J Physiol Endocrinol Metab. 2004 March; 286(3):E321-8) (U.S. Pat. No. 9,364,463).

Baldissarro and colleagues (*The Hip Functional Retrieval after Elective Surgery May Be Enhanced by Supplemented Essential Amino Acids*, Baldissano E, Aquilani R, Boschi F, Baiardi P, Iadarola P, Fumagalli M, Pasini E, Verri M, Dossena M, Gambino A, Cammisuli S, Viglio S. Biomed Res Int. 2016; 2016:9318329) showed improved hip function after hip fracture surgery with 8 g of essential amino acids (eaa) having 1.3% methionine and 0.5% tryptophan.

Dryer and colleagues showed improved total knee replacements (*Essential Amino Acid Supplementation in Patients Following Total Knee Arthroplasty*, Dreyer H C, Strycker L A, Senesac H A, Hocker A D, Smolkowski K, Shah S N, Jewett B A. J Clin Invest. 2013 November; 123(11):4654-66) with an eaa formula after administering 40 g of eaa with only 3% methionine and no tryptophan and no arginine.

U.S. Pat. No. 9,597,367 to Wolfe discloses increasing the amount of tryptophan to 3.1% in a dosage of 22 g/day, while retaining methionine at 3.1%.

Thus, workers in these areas have pursued various directions. It is clear that achieving the best formula for muscle and strength is not obvious, with continuous improvements being made and still being needed during the period extending over at least the last 20 years. Thus, the following is also noted.

Stimulation of protein synthesis is believed to be the metabolic basis for increased muscle strength. An increase in muscle protein synthesis can increase muscle mass, which is related to strength. Increasing muscle protein synthesis also increases muscle protein turnover (i.e., the combination of protein synthesis and breakdown), since the rate of breakdown is believed to be related to the rate of synthesis. Increased muscle protein turnover increases the functioning of muscle fiber units, at least in part because older, damaged proteins are replaced by newly-produced proteins that function more efficiently. Thus, a method to increase protein synthesis could achieve the goal of increasing muscle mass, strength, and physical function.

Further such a method would be important in aging subjects as the rate of muscle loss exceeds the rate of muscle synthesis in subjects older than the late forties, and the ratio of loss/gain continues to degrade with increasing age.

Studies of the acute effects of consuming high amounts of essential and semi-essential amino acids in humans have shown that inclusion, and in some cases increasing their content in the diet can have beneficial effects.

Clinical studies provide evidence that administration of formulas containing essential amino acids and semi-essential amino acids can prevent muscle loss due to aging or bed rest. In particular, studies have shown that these formulas can increase muscle fractional synthetic rate during prolonged bed rest, maintain leg mass and strength during prolonged bed rest, increase lean body mass, improve functional measures of gait and balance, and may serve as a viable intervention for individuals at risk of sarcopenia due to immobility or prolonged bed rest. A major problem in such studies has been the high rate (volume or mass over time) of formula needed to be administered to achieve these results.

Studies on increasing muscle protein anabolism in athletes have shown that formulas containing essential amino acids and semi-essential amino acids provided following exercise promote muscle hypertrophy to a greater extent than that achieved by exercise alone. It has also been shown that formulas containing essential and semi-essential amino acids provided following exercise supports protein synthesis without any increase in protein breakdown, resulting in a net positive protein balance and muscle mass accretion. While muscle protein synthesis appears to respond in a dose-response fashion to essential amino acid supplementation, not all formulas containing essential amino acids and semi-essential amino acids are equal in building muscle.

In cancer in general, protein synthesis is desirable during treatment; both to allow tumor growth, thus improving chemotherapy and radiation-killing of growing tumor cells, and to maintain health.

Skin rejuvenation and wound healing have been proposed to be similar. Growth factors relevant to wound healing stimulate synthesis of new collagen, elastin, and glycosaminoglycans, all of which require a ready pool of amino acids. Skin tone or quality is an extremely desirable attribute, especially in women. It is usually described as skin firmness or skin elasticity or skin texture and is qualified by being visually firmer and resilient.

Skin, hair, and nails are subject to insults by many extrinsic and intrinsic factors. Extrinsic factors include ultra-violet radiation (e.g., from sun exposure), environmental pollution, wind, heat, low humidity, harsh surfactants, abrasives, and the like. Intrinsic factors include chronological aging and other biochemical changes from within the skin, hair, or nails. Whether extrinsic or intrinsic, these factors result in visible signs of skin, hair, and nail aging and environmental damage (e.g., such as sunlight damage, smoke damage, and damage from pollutants such as nitrogen oxides, sulfur oxides, ozone, and metals such as lead). To many people, the loss of the attractiveness of skin, hair, or nails is a reminder of the disappearance of youth. As a result, the maintenance of a youthful appearance is thought to be desirable in youth-conscious societies.

Extrinsic or intrinsic factors may result in the thinning and general degradation of the skin, hair, or nails. For example, as the skin, hair, and nails naturally age, there is a reduction in the cells and blood vessels that supply the skin, hair, or nails. There is also a flattening of the dermal-epidermal junction which results in weaker mechanical resistance of this junction.

The skin ages as a natural consequence of exposure to various environmental factors. Among these factors is exposure to air pollutants, as well as thermal and infra-red radiation. It is reported that over 85% of the visible signs of aging are due to the negative effect of these factors on the skin. Other factors that may play a part in the aging process of the skin include, for example, weathering of the skin, exposure to cigarette smoke and Ultra-Violet (UV) radiation.

Replacement of skin cells slows with aging, and the protein synthesis to adequately protect the skin's collagen and elastin network from the effects of the environmental factors such as those above is highly desirable.

Nutritional compositions are desirable because they are noninvasive and may become a part of an individual's routine without medical supervision.

Proteins normally consist of 20 amino acids, of which 9 are essential in the human: L-histidine, L-isoleucine, L-leucine, L-lysine, L-methionine, L-phenylalanine, L-threonine, L-tryptophan, and L-valine. Additionally L-arginine is a semi-essential amino acid and is used in additional quantities by humans who are attempting to build protein.

The human body requires amino acids for health and/or survival. An estimate of such requirements is as follows (in mg/kg per day, adults): histidine 8-12, isoleucine 10, leucine 14, lysine 12, methionine plus cysteine 13, phenylalanine plus tyrosine 14, threonine 7, tryptophan 3.5 valine 10, (Estimates of Amino Acid Requirements-Recommended Dietary Allowances-NCBI Bookshelf. *Ncbinlmnihgov.* 2017. Available at: https://www.ncbi.nlm.nih.gov/books/NBK234922/table/M00008/?report=objectonly).

Mixtures of amino acids have been given to decrease plasma liver triglycerides. See, e.g., Borsheim, https://www.ncbi.nlm.nih.gov/pmc/articles/PMC2696073/(histidine 3.3%, isoleucine 8.5%, leucine 35.9%, lysine 17.1%, methionine 3.5%, phenylalanine 4.6%, threonine 9.5%, valine 7.5%, arginine 10.0%, however no tryptophan was included in the composition.

Traditionally, desirable mixtures of amino acids, such as mixtures comprising essential amino acids, have been provided by hydrolyzing a protein with relatively high levels of essential amino acids, such as whey protein, and/or by combining free amino acids in a mixture that optionally also includes a hydrolyzed protein such as whey. Mixtures of this type have varying levels of certain amino acids, and no one type of protein has an optimum formula for muscle synthesis, especially in the elderly or the stressed individual.

However, the administration of amino acid compositions is difficult, especially because of difficulties associated with the highly disagreeable taste of some amino acids. For example, compositions using methionine, as well as other amino acids, have been avoided for at least this reason.

An additional difficulty with nutritional supplements for older adults is that older adults generally compensate for increased energy (i.e., calories) delivered by nutritional supplements by reducing food intake. It is therefore desirable to design a supplement that stimulates muscle synthesis more efficiently than food or common protein supplements.

There thus continues to be a need for a nutritional or dietary supplement that can be easily given to individuals in need of addressing the foregoing difficulties.

The need for methods assisting and/or treating individuals in ameliorating such issues also continues.

SUMMARY OF EMBODIMENTS

It has now been found that compositions and methods for increasing strength, muscle mass, functional performance, reducing recovery time after exercise, maintaining muscle strength during exercise, relieving muscle fatigue after exercise, relieving soreness after exercise, and reducing soreness the days following exercise can be provided comprising one or more free essential amino acids, formulated and administered in accordance with the present invention.

It has also now been found that compositions containing a formulation of free essential amino acids comprising at least 5% methionine are of great value in these methods.

The invention provides a nutritional composition comprising: an amino acid component, said amino acid component comprising: L-histidine, L-isoleucine, L-leucine, L-lysine, L-phenylalanine, L-threonine, L-tryptophan, L-valine and L-arginine and at least 7% by weight of L-methionine.

L-methionine may be present in an amount of at least 400 mg methionine per 10 g of said component administered.

The composition can further comprise an additional amino acid selected from the group consisting of L-citrulline, L-cysteine L-carnitine, creatine and mixtures thereof.

L-arginine may be present in an amount of at least 2%, or may be present in an amount of from about 2% to about 50%.

The invention also provides a nutritional composition for improving the health and/or function of a subject in need of such treatment comprising: an amino acid component, said amino acid component including: L-histidine, L-isoleucine, L-leucine, L-lysine, L-phenylalanine, L-threonine, L-tryptophan, L-valine and L-arginine and L-methionine, based on the total weight of amino acid component, wherein the amount of L-methionine is at least 9%, composing more than 400 mg of L-methionine per 10 g/serving and the amount of L-tryptophan is greater than 3% based on the total weight of the amino acid component.

The invention also provides a method of reducing recovery time after exercise, maintaining muscle strength during exercise, relieving muscle fatigue after exercise, relieving soreness after exercise, and reducing soreness the days following exercise, comprising: generating a composition of matter comprising at least 5% methionine by weight % of the total essential amino acids present in the composition and to provide the recipient the composition of matter.

The invention also provides a method of reducing recovery time after exercise, maintaining muscle strength during exercise, relieving muscle fatigue after exercise, relieving soreness after exercise, and reducing soreness the days following exercise, comprising: generating a composition of matter comprising at least 5% methionine and a sweetener, along with flavorings and liquids, chosen by the patient or provided in the composition, to provide the recipient the composition of matter in a palatable, liquid form or a solid edible form.

The invention also provides a method reduction in scar coloration, improving scar appearance, during and after healing and reducing recovery time for scar healing after surgery, comprising: generating a composition of matter comprising at least 5% methionine by weight % of the total essential amino acids present in the composition and to provide the recipient the composition of matter.

Also provided is a method of improving skin firmness, elasticity and texture and providing skin that is visually firmer and more resilient comprising: generating a composition of matter comprising at least 5% methionine and a sweetener, along with flavorings and liquids, chosen by the patient or provided in the composition, to provide the recipient the composition of matter in a palatable form.

Thus, a method to increase protein synthesis is provided by the invention which aims to achieve the goal of improving skin firmness, elasticity and texture and providing skin that is visually firmer and more resilient.

A method to increase protein synthesis could achieve the goal of improving wound healing time and surgical recovery time and outcome, as well as reducing cancer cachexia, while maintaining these improvements during treatment, and the invention addresses this need.

Nutritional compositions currently designed to specifically promote muscle protein synthesis in elderly individuals, or more generally to improve strength and functional performance in elderly individuals require high levels of intake of essential amino acids because they do not contain a balanced formula and have low levels of certain amino acids, especially methionine, which limits the value of the other amino acids in the composition. Current nutritional compositions used to increase strength, muscle mass and performance, are not believed to have sufficient methionine to effectively accomplish the goals stated herein, alone or in combination with muscle-building compounds such as creatine. For example, whey isolates contain about 2-3% methionine, which limits the use of other essential amino acids in the mixture, giving lower protein synthesis than expected from the total quantity of essential amino acids given to achieve improved muscle mass, strength, and functional performance. These limitations are overcome by the present invention.

It is thought that skin aging is similar to a wound, capable of overwhelming the skin's repair mechanisms, which become attenuated with age due to lack of stimulation by growth hormones. Once skin injury has occurred, the body starts a wound healing response to promote new cell growth and to decrease wound contraction and scarring, all of which are dependent on an abundant source of essential and semi-essential amino acids. What has been needed, and heretofore been unavailable, is a method of skin care that assists in rejuvenating the skin and reversing the signs of aging caused by exposure to environmental factors, such as those found during the day. The present invention addresses and satisfies these and other needs.

In certain embodiments, the invention provides a composition of matter for increasing muscle mass, strength, and functional performance, comprising: an amino acid component, said amino acid component including: at least 5 percent by weight L-methionine of the total essential amino acids present; and at least one other amino acid, said other amino acid selected from the group consisting of: L-histidine, L-isoleucine, L-leucine, L-phenylalanine, L-threonine, L-tryptophan, and L-valine.

The compositions may comprise the following concentrations of essential amino acids in terms of w/w %: L-histidine, 3-9%; L-isoleucine, 4-11%; L-leucine, 3-37%; L-lysine, 4-12%; L-methionine, 5-17%; L-phenylalanine, 6-17%; L-threonine, 0.3-9%; L-tryptophan, 1-4%; L-valine, 4-19%; and L-arginine, 0-60%.

In embodiments, the invention provides compositions comprising: an amino acid component, said amino acid component including: L-histidine, L-isoleucine, L-leucine, L-lysine, L-phenylalanine, L-threonine, L-tryptophan, L-valine and L-arginine and at least 5 percent by weight L-methionine. Arginine may be replaced by citrulline or combinations thereof or other amino acids.

In embodiments, the invention provides a composition of matter for increasing muscle mass, strength, and functional performance, comprising: an essential amino acid component, said essential amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine and the semi-essential amino acid L-arginine. Arginine may be replaced by citrulline or combinations thereof or other amino acids.

In embodiments, the invention provides a composition of matter for reducing recovery time after exercise, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for relieving muscle fatigue after exercise, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for relieving soreness after exercise, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for reducing soreness the days following exercise, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for maintaining muscle mass after bariatric surgery, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for treating sarcopenia, comprising: an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine and L-arginine. Arginine may be replaced by citrulline or combinations thereof or other amino acids.

In embodiments, the invention provides a composition of matter for maintaining muscle mass, strength, and functional performance during cancer treatment and surgery, comprising: an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, and L-valine.

In embodiments, the invention provides a composition of matter for maintaining muscle mass, strength, and functional performance during cancer treatment and surgery, comprising: an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine, and L-arginine. Arginine may be replaced by citrulline or combinations thereof or other amino acids.

In embodiments, the invention provides a composition of matter for improving wound outcomes in surgical incisions, chronic wounds and radiation injury, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for improving surgical recovery time, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for reduction in scar tissue following injury or wound outcomes in surgical incisions, chronic wounds and radiation injury, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for improving scar appearance outcomes in surgical incisions, chronic wounds, radiation injury and trauma, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for reduction in scar tissue following injury or wound outcomes in surgical incisions, chronic wounds and radiation injury, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition of matter for reduction in scar coloration during and after healing, comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine.

In embodiments, the invention provides a composition of matter for improving skin tone comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, the invention provides a composition for improving acne comprising: an amino acid component, said amino acid component selected from the group consisting of: L-histidine, L-isoleucine, L-leucine, L-lysine, L-methionine, L-phenylalanine, L-threonine, L-tryptophan, L-valine and L-arginine. Arginine may be replaced by citrulline or combinations thereof or other amino acids.

In embodiments, any of the foregoing can comprise an amino acid mixture containing: L-histidine, L-isoleucine, L-leucine, L-lysine, L-methionine, L-phenylalanine, L-threonine, L-tryptophan, L-valine and L-arginine, having at least 5% methionine, 0.5% arginine, and 0.3% leucine by weight of the total essential and semi-essential amino acids present.

In embodiments, the invention provides a such compositions comprising the following concentrations of amino acids in terms of w/w %: L-histidine, 3-9%; L-isoleucine, 4-11%; L-leucine, 3-28%; L-lysine, 4-12%; L-methionine, 5-17%; L-phenylalanine, 6-17%; L-threonine, 2-9%; L-tryptophan, 1-4%; L-valine, 4-19% and L-arginine, 0-60%.

In embodiments, the invention provides a composition comprising the following concentrations of amino acids in terms of w/w %: L-histidine, 4.3%; L-isoleucine, 5.6%; L-leucine, 8.7%; L-lysine, 6.3%; L-methionine, 8.7%; L-phenylalanine, 8.7%; L-threonine, 3.9%; L-tryptophan, 2.0%; L-valine, 6.3% and L-arginine, 45.5%.

In embodiments, the invention provides a composition comprising the following concentrations of amino acids in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6% and L-arginine, 35.2%.

In embodiments, the invention provides a composition comprising the following concentrations of amino acids in terms of w/w %: L-histidine, 5.1%; L-isoleucine, 6.5%; L-leucine, 37.0%; L-lysine, 7.4%; L-methionine, 10.1%; L-phenylalanine, 10.1%; L-threonine, 4.5%; L-tryptophan, 2.4%; L-valine, 7.4%; and L-arginine, 9.4%.

In embodiments, the invention provides a composition comprising the following concentrations of amino acids in terms of w/w %: L-histidine, 4.1%; L-isoleucine, 5.2%; L-leucine, 29.5%; L-lysine, 5.9%; L-methionine, 8.1%; L-phenylalanine, 8.1%; L-threonine, 3.6%; L-tryptophan, 1.9%; L-valine, 5.9%; and L-arginine, 27.6%.

In embodiments, the invention provides a composition comprising the following concentrations of amino acids in terms of w/w %: L-histidine, 4.1%; L-isoleucine, 5.2%; L-leucine, 29.5%; L-lysine, 5.93%; L-methionine, 8.1%; L-phenylalanine, 8.1%; L-threonine, 3.6%; L-tryptophan, 1.9%; L-valine, 5.9% and L-arginine, 27.6%.

In embodiments, the invention provides such a composition comprising an amino acid mixture wherein a keto acid has been substituted for the corresponding amino acid.

In embodiments, the invention provides such a composition comprising an amino acid mixture wherein a hydroxy acid has been substituted for the corresponding amino acid.

In embodiments, the invention provides such a composition comprising an amino acid mixture wherein a semi-essential amino acid selected from the group consisting of arginine, citrulline, cysteine, glycine, glutamine, proline, and tyrosine or their immediate biosynthetic precursor amino acid has been added to the essential amino acids.

In embodiments, the invention provides such a composition comprising an amino acid mixture wherein a non-standard amino acid selected from the group consisting of L-carnitine, GABA, hydroxyproline, hydroxylysine, pyrrolysine, selenomethionine, hypusine, L-DOPA, 2-aminobutyric acid, dehydralanine, and gamma-carboxyglutamic acid has been added to the essential amino acids.

In embodiments, the invention provides such a composition wherein the composition is provided as a component of means for liquid or edible administration. Any of the foregoing compositions can further comprise an excipient.

In aspects the invention also provides a method for maintaining muscle mass, strength, and functional performance, comprising: providing a composition of matter comprising an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, and L-valine; and providing to a patient said composition of matter.

Also provided is a method for maintaining muscle mass, strength, and functional performance, comprising: providing a composition of matter comprising an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine, and L-arginine; and providing to a patient said composition of matter.

A method for relieving muscle fatigue after exercise is also provided comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

Also provided is a method for relieving soreness after exercise, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for reducing soreness the days following exercise, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for maintaining muscle mass, strength, and functional performance during cancer treatment and surgery, comprising: providing a composition of matter comprising an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, and L-valine; and providing to a patient said composition of matter.

In embodiments, the invention also provides a method for maintaining muscle mass, strength, and functional performance during cancer treatment and surgery, comprising: providing a composition of matter comprising an amino acid component, said amino acid component including: at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine, and L-arginine; and providing to a patient said composition of matter.

In embodiments, the invention also provides a method for improving wound healing, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving wound outcomes in surgical incisions, chronic wounds and radiation injury, and recovery time from such, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving surgical recovery time, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving scar appearance after surgical incisions, chronic wounds and radiation injury, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for reduction in scar tissue following injury, surgical incisions, chronic wounds and radiation injury, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving a subject wherein the subject is at least one of: elderly, critically-medically ill, frail, obese, or suffering from protein-energy malnutrition, cachexia, sarcopenia, skin ulcerations, osteoporosis, chronic obstructive pulmonary disease, chronic heart failure, HIV, polio, Guillain-Barre syndrome, congestive heart failure, acute coronary syndrome, cancer, spinal cord injury, osteoarthritis, arthritis, stroke, Parkinson's disease, Alzheimer's disease, dementia, malnutrition, muscular dystrophy, spinal muscular atrophy, inflammatory myopathy, a disease of the peripheral nerve, fibromyalgia, neuropathy, a disease of the neuromuscular junction, and a metabolic disease of the muscle or other disease states, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for reduction in scar coloration during and after healing of surgical incisions, chronic wounds, radiation injury and trauma, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving skin tone comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides a method for improving acne, comprising: providing a composition of matter comprising an amino acid component, said amino acid component selected from the group consisting of: L-histidine, L-isoleucine, L-leucine, L-lysine, L-methionine, L-phenylalanine, L-threonine, L-tryptophan, L-valine and L-arginine; and providing to a patient said composition of matter.

In embodiments, the invention also provides such methods employing a composition comprising the following concentrations of amino acids in terms of w/w %: L-histidine, 8.0%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%.

In embodiments, the invention also provides such methods, wherein the amino acid component comprises: L-histidine, L-isoleucine, L-leucine, L-lysine, L-methionine, L-phenylalanine, L-threonine, L-tryptophan, L-valine and L-arginine, having at least 5% methionine, and 5% arginine by weight of the total essential and semi-essential amino acids present.

Also in embodiments, such methods employ an amino acid component comprising concentrations of amino acids in terms of w/w %: L-histidine, 1.9-9%; L-isoleucine, 4-11%; L-leucine, 3-28%; L-lysine, 4-12%; L-methionine, 5-17%; L-phenylalanine, 6-17%; L-threonine, 0.3-9%; L-tryptophan, 1-4%; L-valine, 4-19%; and L-arginine, 0-60%.

In embodiments, the invention provides a such methods wherein the amino acid component the following concentrations of amino acids in terms of w/w %: L-histidine, 5.1%; L-isoleucine, 6.5%; L-leucine, 37.0%; L-lysine, 7.4%; L-methionine, 10.1%; L-phenylalanine, 10.1%; L-threonine, 4.5%; L-tryptophan, 2.4%; L-valine, 7.4%; and L-arginine, 9.4%.

In embodiments, the invention provides such methods wherein the amino acid component comprising the following concentrations of amino acids in terms of w/w %: L-histidine, 4.1%; L-isoleucine, 5.2%; L-leucine, 29.5%; L-lysine, 5.9%; L-methionine, 8.1%; L-phenylalanine, 8.1%; L-threonine, 3.6%; L-tryptophan, 1.9%; L-valine, 5.9%; and L-arginine, 27.6%.

In embodiments, the invention also provides such methods wherein the amino acid component comprises the following concentrations of amino acids in terms of w/w %: L-histidine, 4.3%; L-isoleucine, 5.6%; L-leucine, 8.7%; L-lysine, 6.3%; L-methionine, 8.7%; L-phenylalanine, 8.7%; L-threonine, 3.9%; L-tryptophan, 2.0%; L-valine, 6.3%; and L-arginine, 45.5%.

In embodiments, such methods may employ such an amino acid component comprising the following concentrations of amino acids in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6%; and L-arginine, 35.2%.

In embodiments, the invention also provides such methods wherein the amino acid component comprises the following concentrations of amino acids in terms of w/w %: L-histidine, 4.1%; L-isoleucine, 5.2%; L-leucine, 29.5%; L-lysine, 5.93%; L-methionine, 8.1%; L-phenylalanine, 8.1%; L-threonine, 3.6%; L-tryptophan, 1.9%; L-valine, 5.9% and L-arginine, 27.6%.

In some such methods a dose of 1.5 g to 42 g of the said amino acid component is administered to a human subject one, two, or three times a day and/or such doses taken over a 24 hour period.

In some such methods the dose of methionine in either D or L configuration or a mixture thereof, or the hydroxyl analog thereof is at least 200 mg.

In some such methods the dose of L-tryptophan is at least 50 mg.

The amino acid component may further comprise an excipient.

In embodiments, the administration may be oral.

In embodiments, the administration may be made in liquid form.

In embodiments, the administration may be made in edible form.

In embodiments, the invention also provides such methods comprising administering an amino acid component, a chewable form containing carrageenan, an organic acid, a sweetener, an oil, glycerol, flavors and an excipient.

In each of the foregoing methods, improvement is noted relative to, or in comparison with the stated indication or condition in a subject who has not had the composition of the invention administered.

Other exemplary embodiments and advantages of the present invention may be ascertained or will be apparent to those of skill in the art upon reviewing the present disclosure.

DETAILED DESCRIPTION OF EMBODIMENTS

The particulars shown herein are by way of example and for purposes of illustrative discussion of the embodiments of the present invention only and are presented in an effort to provide what is believed to be the most useful and readily understood description of the principles and conceptual aspects of the present invention. In this regard, no attempt is made to show structural or other details of the present invention in more detail than is necessary for the fundamental understanding of the present invention, the description taken making apparent to those skilled in the art how the several forms of the present invention may be embodied in practice.

It has now been found that compositions containing the essential amino acids and increased and/or optimized amounts of methionine and, optionally, an additional amino acid, are useful in addressing and ameliorating the conditions described herein.

The amount of the additional amino acid may also be optimized.

In certain embodiments, the additional amino acid may be tryptophan.

Additionally, it has been found that compositions containing the essential amino acids and also containing arginine are useful in addressing and ameliorating the conditions described herein. It has further been found that such compositions containing increased and/or optimized amounts of arginine and leucine are particularly useful.

Such compositions can include increased and/or optimized amounts of one or more of methionine, tryptophan, arginine and leucine.

Further, it has now been found that compositions containing the essential amino acids, an increased or optimized amount of methionine and one or more of an additional amino acid, such as any of tryptophan, arginine, citrulline, and/or cysteine are particularly useful.

Such compositions would be expected to be avoided by skilled workers in the art, especially because of the well-known disagreeable taste of a number of the EAA.

Compositions and methods of the invention improve wound healing, improve surgical recovery time, and reduce scar tissue following injury. The compositions generally comprise a blend of amino acids, containing at least 5% methionine in which the proportion of each amino acid is tailored to optimize muscle protein synthesis. Such compositions may also contain essential amino acids, semi-essential amino acids (e.g., conditional amino acids), non-essential amino acids and their hydroxy analogs and keto analogs.

The compositions may contain at least 7% methionine.

In one embodiment of such compositions, the methionine comprises a percentage of the composition by mass between about 5 and about 20 percent, more preferably between about 5 and about 18 percent, and more preferably between about 5 and about 15 percent.

In an embodiment, such a composition is in a composition for liquid administration.

In a still further embodiment, the composition further comprises an excipient.

In an embodiment of the method the patient is elderly and the method of delivering may be oral, such as through liquid or edible administration.

In a still further embodiment of the method the providing is oral, such as by liquid administration, chewable bite, such as in U.S. Pat. No. 7,223,417, by capsule or by tube. U.S. Pat. No. 7,223,417 is hereby incorporated by reference, as though set forth in full herein, especially for its disclosure of how to prepare suitable, palatable oral formulations.

The method also improves outcomes after gastric restrictions, such as gastric bypass or sleeve (also called bariatric surgery), where the maintenance of muscle mass during weight loss is desirable in both young and old individuals.

Further, the method provides an easier method to obtain protein building blocks after gastric restrictions, such as gastric bypass or sleeve, where the maintenance of muscle mass during weight loss is desirable and the volume of solids is limited. As the composition of this invention is soluble in water, it is easily processed by the bariatric patient and has a very low caloric value.

Recovery time after exercise, maintaining muscle strength during exercise, relieving muscle fatigue after exercise, relieving soreness after exercise, reducing soreness the days following exercise, may be improved by stimulating muscle protein synthesis. Disclosed herein are compositions and methods that reduce recovery time after exercise, maintain muscle strength during exercise, relieve muscle fatigue after exercise, relieve soreness after exercise, and reduce soreness the days following exercise. The compositions generally consist of a blend of amino acids, containing at least 5% methionine in which the proportion of each amino acid is tailored to optimize muscle protein synthesis. Such compositions may also contain essential amino acids, semi-essential amino acids, non-essential amino acids and their hydroxy analogs and keto analogs.

Generally, compositions of the invention address all the aspects of protein synthesis including providing all of the essential amino acids at levels known to be required for optimal protein synthesis. While certain aspects of the levels required protein synthesis are known, how to provide such levels by administering an optimal blend of amino acids has not been known heretofore. The availability of the essential amino acids which are not produced by the body will be increased by ingestion of the composition. Energy may be provided by low-glycemic carbohydrates that may induce a minimal insulin response. In an embodiment, such energy is provided in the amounts needed.

Without wishing to be bound by theory, it is thought that the rationale underlying the compositions disclosed herein relates to both the individual effects of the components and their interactive effects. The amino acids must be in a balanced formula containing sufficient amounts of both lysine and methionine, essential amino acids which are known to be limiting in stimulating protein synthesis, especially when the intake of extracorporeal methionine is limited. The particular essential amino acids are provided because they cannot be produced in the body and thus their availability is rate-limiting for protein synthesis. Arginine is normally produced in adequate quantities in the body, but endogenous production may be limited due to trauma, surgery, reduction of protein intake as in bariatric surgery or in the elderly. Amino acids are preferably included in the free form, but may also be included in combinations of peptides; in combinations of intact protein and free amino acids; in combinations of free amino and peptides; or in combinations of free amino acids, peptides, and proteins.

In general, compositions of the invention may be optimized by optimizing the content of a limiting amino acid, and balancing the content of the remaining amino acids around this optimization. It is well known that plant proteins are low in methionine and lysine, and each of these can be added to raise the amount of nitrogen use in a feedstock for non-ruminant animals. In human nutrition, it has been assumed for many years that ample supplies of limiting amino acids would be available from ingested protein in the diet. The present results have shown that this assumption made in 100's of medical literature papers on the subject of stimulation of protein is in error and that the use of higher levels of these compounds in the compositions herein were completely unexpected to be efficacious or even necessary by the medical nutritional research community.

One embodiment encompasses a composition comprising L-histidine, L-isoleucine, L-leucine, L-valine, L-lysine, L-methionine, L-phenylalanine, L-threonine, L-arginine, hydroxy methionine, or the keto analogs of the amino acids.

The concentrations of the other amino acids may be in any proportion to optimize muscle protein synthesis. The concentration of L-methionine in the composition is to be above 5% by mass of the essential and nonessential amino acids present. The concentration of L-histidine in the composition may be between 1.9 and 10% by weight of the amino acids. The concentration of L-phenylalanine in the composition may be between 5 and 17% of the amino acids by mass. The concentration of L-threonine in the composition may be about between 2 and 10% of the amino acids by mass. The concentration of L-valine may be between 4 and 12% by mass of the amino acids. The concentration of L-isoleucine may be between 4 and 12% by mass of the amino acids. The concentration of L-lysine in the composition may be between 4 and 12% of the amino acids by mass. The L forms of the amino acids are the naturally occurring isomers normally present in the body.

In a preferred embodiment, the following components have the following percentages of the total amino acids by mass: L-histidine, 4.1; L-isoleucine, 5.2; L-leucine, 29.5; L-lysine, 5.9; L-methionine, 8.1; L-phenylalanine, 8.1; L-threonine, 3.6; L-tryptophan, 1.9; L-valine, 5.9; and L-arginine, 27.6.

In some embodiments, the composition comprises about 5, 5.1, 5.2, 5.3, 5.4, 5.5, 5.6, 5.7, 5.8, 5.9, 6, 6.1, 6.2, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, or about 17 w/w % of methionine.

In some embodiments, the composition comprises about 2%, to about 5 w/w % of tryptophan.

In some embodiments, the composition comprises about 2, or about 50 w/w % of arginine.

In some embodiments, the composition comprises about 5%, or about 50% w/w % of leucine.

In a further embodiment, carbohydrates may comprise up to twice the total mass of histidine, isoleucine, leucine, lysine, methionine, phenylalanine, threonine, tryptophan, and valine.

In another embodiment arginine may range from about 0-50% of the amino acids. Methionine may range from about 5-17% by mass of the amino acids, and the low glycemic carbohydrate may range from about 0-50% of the total mass. The other amino acids may be in proportion to optimize muscle protein synthesis In an embodiment, a plurality of amino acids comprises one or more essential amino acids. Applicant has found the preferential use of essential amino acids compared to non-essential amino acids in a combination of the invention reduces the amount of amino acids that must be given to elicit an effective response. An essential amino acid is an amino acid that cannot be synthesized de novo by a subject, and therefore must be supplied in its diet.

A semi-essential amino acid is an amino acid that is considered conditionally essential in the human diet, meaning its synthesis can be limited under special pathophysiological conditions such as severe catabolic distress. Six amino acids are considered conditionally essential in the human diet, meaning their synthesis can be limited under special conditions. These six are arginine, cysteine, glycine, glutamine, proline, and tyrosine.

In some embodiments, a combination of the invention comprises phenylalanine, valine, threonine, tryptophan, methionine, leucine, isoleucine, lysine, and histidine. In other embodiments, a combination of the invention comprises phenylalanine, valine, threonine, tryptophan, methionine, leucine, isoleucine, lysine, histidine and a conditionally essential amino acid. In other embodiments, a combination of the invention comprises phenylalanine, valine, threonine, tryptophan, methionine, leucine, isoleucine, lysine, histidine and arginine.

When a combination of the invention comprises all nine essential amino acids and other amino acids, the nine essential amino acids are at least about 70% of the total weight of the combination. In yet another alternative, the nine essential amino acids can be about 50% to about 100% of the total weight of the combination.

In another embodiment, a combination of the invention has a higher proportion of methionine compared to the total amount of all the essential amino acids in the combination than used by previous investigators in the medical and patent literature.

In another embodiment, the percentage of the total essential amino acids plus semi-essential amino acids or other amino acids, is about 5 to 50% by weight of all the essential amino acids and semi-essential amino acids.

In another embodiment, a plurality of amino acids comprises one or more non-standard amino acid. As used herein, the term "non-standard amino acid" refers to a non-proteinogenic amino acid that occurs naturally in a cell. In a cell, a non-standard amino acid is generated by modification of a proteinogenic amino acid. Non-limiting examples of non-standard amino acids include L-carnitine, GABA, hydroxyproline, hydroxylysine, pyrrolysine, selenomethionine, hypusine, L-DOPA, 2-aminobutyric acid, dehydralanine, gamma-carboxyglutamic acid. In some embodiments, a combination of the invention comprises phenylalanine, valine, threonine, tryptophan, methionine, leucine, isoleucine, lysine, histidine, and at least one non-standard amino acid.

In another embodiment, the nutritional compositions include essential amino acids and may include other functional ingredients such as, but not limited to probiotics and branched chain fatty acids.

In an embodiment, combinations of the invention further comprise at least one nutrient selected from the group consisting of omega-3 fatty acids and biotin. In other preferred embodiments, combinations of the invention further comprise two nutrients selected from the group consisting of omega-3 fatty acid and biotin. The overall contribution of the one or more nutrients to the total weight of the combination in such cases is substantially less than the contribution of the plurality of amino acids. Generally, the one or more nutrients comprise no more than about 10% by weight, preferably no more than about 5% by weight, more preferably no more than about 3% by weight of the combination. In preferred embodiments, the one or more nutrient is biotin. In other preferred embodiments, the one or more nutrient is one or more omega-3 fatty acids. In other preferred embodiments, the one or more nutrient is biotin and one or more omega-3 fatty acids.

In other embodiments, a combination of the invention comprises (i) phenylalanine, valine, threonine, tryptophan, at least 5% methionine, leucine, isoleucine, lysine, and histidine; (ii) at least one conditionally essential amino acid; and (iii) at least one non-standard amino acid. In still other embodiments, a combination of the invention comprises (i) phenylalanine, valine, threonine, tryptophan, at least 5% methionine, leucine, isoleucine, lysine, and histidine; (ii) at least one conditionally essential amino acid precursor; and (iii) at least one non-standard amino acid. In yet other embodiments, a combination of the invention comprises (i) phenylalanine, valine, threonine, tryptophan, methionine, leucine, isoleucine, lysine, and histidine; (ii) at least one conditionally essential amino acid; (iii) at least one conditionally essential amino acid precursor; and (iv) at least one non-standard amino acid. In other embodiments, the conditionally essential amino acid is arginine or citrulline and the non-standard amino acid is L-carnitine.

Keto acids or ketoacids (also called oxo acids or oxoacids) are organic compounds that contain a carboxylic acid group and a ketone group. The keto acids are precursors of the amino acids in the human, specifically, valine derives from the amination of alpha-ketoisovaleric acid; phenylalanine derives from the amination of phenylpyruvic acid; methionine derives from the amination of alpha-ketogamma-methylthiobutyric acid; leucine derives from the amination of alpha-ketoisocaproic acid; isoleucine derives from the amination of alpha-keto-beta-methylvaleric acid; histidine derives from the amination of imidazolepyruvic acid; tryptophan derives from the amination of indolepyruvic acid; lysine derives from the amination of alpha-keto-gamma-aminocaproic acid; and threonine derives from the amination of alpha-keto-beta-hydroxybutyric acid. These transformations are known to take place readily in the body and one or more of the keto-analogs of the amino acids may be used in place of the amino acids of the invention.

The hydroxy-acid analogs of methionine, phenylalanine and isoleucine are also effective in the body and may be used in the invention in place of their respective amino acids.

In one embodiment of the invention, the composition of matter for increasing muscle mass, strength, and functional performance comprises at least 5 percent by weight L-methionine of the total essential amino acids present and at least one other amino acid, selected from the group consisting of: L-histidine, L-isoleucine, L-leucine, L-lysine, L-phenylalanine, L-threonine, L-tryptophan, L-valine and L-arginine.

In another embodiment of the invention, the amino acid mixture may contain L-histidine, L-isoleucine, L-leucine, L-lysine, L-methionine, L-phenylalanine, L-threonine, L-tryptophan, L-valine and L-arginine, having at least, 5% methionine, 5% arginine, and 3% leucine by weight of the total essential and semi-essential amino acids present.

In another embodiment of the invention, the amino acid mixture comprises the following concentrations of amino acids in terms of w/w %: L-histidine, 3-9%; L-isoleucine, 4-11%; L-leucine, 3-28%; L-lysine, 4-12%; L-methionine, 5-17%; L-phenylalanine, 0.3-17%; L-threonine, 2-9%; L-tryptophan, 1-4%; L-valine, 4-19% and L-arginine, 0-60%.

In another embodiment of the invention, the amino acid mixture may contain the following concentrations of amino acids in terms of w/w %: L-histidine, 8.0%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%.

In another embodiment of the invention, the amino acid mixture comprises the following concentrations of amino acids in terms of w/w %: L-histidine, 4.3%; L-isoleucine, 5.6%; L-leucine, 8.7%; L-lysine, 6.3%; L-methionine, 8.7%; L-phenylalanine, 8.7%; L-threonine, 3.9%; L-tryptophan, 2.0%; L-valine, 6.3% and L-arginine, 45.5%.

In another embodiment of the invention the amino acid mixture comprises the following concentrations of amino acids in terms of w/w %: L-histidine, 5.1%; L-isoleucine, 6.5%; L-leucine, 37.0%; L-lysine, 7.4%; L-methionine, 10.1%; L-phenylalanine, 10.1%; L-threonine, 4.5%; L-tryptophan, 2.4%; L-valine, 7.4%; and L-arginine, 9.4%.

In another embodiment of the invention, the amino acid mixture comprises the following concentrations of amino acids in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6% and L-arginine, 35.2%.

In another embodiment of the invention, the amino acid mixture comprises the following concentrations of amino acids in terms of w/w %: L-histidine, 4.1%; L-isoleucine, 5.2%; L-leucine, 29.5%; L-lysine, 5.93%; L-methionine, 8.1%; L-phenylalanine, 8.1%; L-threonine, 3.6%; L-tryptophan, 1.9%; L-valine, 5.9% and L-arginine, 27.6%.

In another embodiment of the invention, the amino acid mixture may contain a component of means for liquid administration.

In another embodiment of the invention, the amino acid mixture may contain an excipient.

In another embodiment of the invention, the amino acid mixture may contain amino acids selected from the group consisting comprising: L-histidine, L-isoleucine, L-leucine, L-lysine, L-methionine, L-phenylalanine, L-threonine, L-tryptophan, L-valine and L-arginine.

In another embodiment of the invention, the amino acid mixture may contain concentrations of amino acids in terms of w/w %: L-histidine, 8.0%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%.

In another embodiment of the invention for relieving muscle fatigue after exercise, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for relieving soreness after exercise, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving scar appearance outcomes in surgical incisions, chronic wounds, radiation injury and trauma, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for reduction in scar coloration during and after healing, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for reducing wrinkling or fine lines in skin, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving acne in persons suffering from acne, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving scar appearance after surgical incisions, chronic wounds and radiation injury trauma, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention for reduction in scar tissue following injury, surgical incisions, chronic wounds and radiation injury, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention for reduction in scar coloration during and after healing of surgical incisions, chronic wounds, radiation injury and trauma, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention a method is provided for improving skin tone and reducing wrinkling and fine lines in skin in which a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention for improving acne in persons suffering from acne, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention for reducing soreness in the days following exercise the amino acid mixture comprises L-histidine, L-isoleucine, L-leucine, L-lysine, L-methionine, L-phenylalanine, L-threonine, L-tryptophan, L-valine and L-arginine.

Further, the method improves outcomes after gastric restrictions, such as gastric bypass or sleeve, where the maintenance of muscle mass during weight loss is desirable in both young and old individuals. In an embodiment of the invention for maintaining muscle mass after bariatric surgery, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for treating sarcopenia, the amino acid mixture comprises at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine and L-arginine.

In another embodiment of the invention for relieving muscle fatigue after exercise a patient may be provided a mixture of L-histidine, L-isoleucine, L-leucine, L-lysine, L-methionine, L-phenylalanine, L-threonine, L-tryptophan, L-valine and L-arginine.

Surgery introduces a need for the healing of the surgical wound, both internally and externally. Often, especially after the introduction of an implant, the time to normal function (recovery time) is extended by the need for the body to accommodate itself to an implant. The rapid restoration of the tissue surrounding the implant is desirable. It is especially desirable that surface (skin) healing be rapid, without accumulation of excess scar tissue, and that the appearance of the healed area have minimal differences from the surrounding tissue in both appearance and feel. It is important that scar tissue be minimized, both internally and externally.

In another embodiment of the invention for improving surgical recovery time, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving outcomes in surgical incisions, chronic wounds and radiation injury, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving healing in ulcers, the amino acid mixture comprises L-histidine, L-isoleucine, L-leucine, L-lysine, L-methionine, L-phenylalanine, L-threonine, L-tryptophan, L-valine and L-arginine.

In another embodiment of the invention for improving wound healing a patient may be provided a mixture of L-histidine, L-isoleucine, L-leucine, L-lysine, L-methionine, L-phenylalanine, L-threonine, L-tryptophan, L-valine and L-arginine.

In another embodiment of the invention for improving wound outcomes in surgical incisions, chronic wounds and radiation injury recovery time, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention for reduction in scar tissue following injury, surgical incisions, chronic wounds and radiation injury, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention the subject has at least one of: osteoporosis, chronic obstructive pulmonary disease, Duchenne's Muscular Dystrophy, cystic fibrosis, chronic heart failure, HIV, polio, Guillain-Barre syndrome, congestive heart failure, acute coronary syndrome, cancer, spinal cord injury, osteoarthritis, arthritis, stroke, malnutrition, muscular dystrophy, spinal muscular atrophy, inflammatory myopathy, a disease of the peripheral nerve, fibromyalgia, neuropathy, Parkinson's disease, Alzheimer's disease, a disease of the neuromuscular junction, a metabolic disease of the muscle or other disease states and is provided a mixture comprising L-histidine, L-isoleucine, L-leucine, L-lysine, L-methionine, L-phenylalanine, L-threonine, L-tryptophan, L-valine and L-arginine.

In another embodiment of the invention for relieving soreness after exercise, a patient may be provided a mixture of L-histidine, L-isoleucine, L-leucine, L-lysine, L-methionine, L-phenylalanine, L-threonine, L-tryptophan, L-valine and L-arginine.

In another embodiment of the invention for reducing soreness the days following exercise, a patient may be provided a mixture of L-histidine, L-isoleucine, L-leucine, L-lysine, L-methionine, L-phenylalanine, L-threonine, L-tryptophan, L-valine and L-arginine.

In another embodiment of the invention for treating sarcopenia, a patient may be provided a mixture comprising at least 5 percent by weight L-methionine of the total essential amino acids present; and at least one other amino acid, said other amino acid selected from the group consisting of: L-histidine, L-isoleucine, L-leucine, L-lysine, L-phenylalanine, L-threonine, L-tryptophan, L-valine and L-arginine.

In another embodiment of the invention for reducing recovery time after exercise, a patient may be provided a mixture comprising L-histidine, L-isoleucine, L-leucine, L-lysine, L-methionine, L-phenylalanine, L-threonine, L-tryptophan, L-valine and L-arginine.

In another embodiment of the invention the subject treated is elderly, suffering from protein-energy malnutrition, cachexia, or sarcopenia, and is provided a mixture comprising L-histidine, L-isoleucine, L-leucine, L-lysine, L-methionine, L-phenylalanine, L-threonine, L-tryptophan, L-valine and L-arginine.

As will be appreciated by one of skill in the art, the dose (also referenced herein as serving amount or amount administered, e.g., administration) of the amino acid composition of the invention can and will vary depending on the body weight, sex, age and/or medical condition of the subject, the intensity of the physical exercise, the length of bed rest, the severity of the muscle damage or trauma suffered by the subject, the method of administration, and the duration of rehabilitation. Routine experimentation may readily establish the required dosage. The dosage of the compositions according to the invention generally is from about 20 to about 1000 mg/kg of body weight/day, preferably 40 to 350 mg/kg of body weight. In accordance with the invention, 10.5 g-31.5 g/day for an average size person (154 lb) is typical. Typical doses of the amino acid composition of the invention for oral administration may be about 1.5 g per dose. In some embodiments, a dose of about 1, 2, 2.5, 3, 3.5, 5, 4, 4.5, 5, or 5.5 g of the amino acid composition may be administered. In other embodiments, a dose of about 6, 7, 8, 9, 10, 11, 12, 13, 14, 15, 16, 17, 18, 19 or 20 g of the amino acid composition may be administered. In yet other embodiments, a dose of about 20, 21, 22, 23, 24, 25, 26, 27, 28, 29, 30, 31, 32, 33, 34, 35, 36, 37, 38, 39, 40, 41 or 42 g of the amino acid composition may be administered each day. In an exemplary embodiment, the amino acid dose may be about 3.5 g per dose.

In embodiments, the dose contains about 400 mg methionine per dose. 101.991 In a preferred embodiment of the invention, a 1.5 g dose of the composition is administered to a human subject one, two, or three times a day. In an embodiment of the invention, a 6 g dose of the composition is administered to a human subject one, two, or three times a day. In an embodiment of the invention, an 11 g dose of the composition is administered to a human subject one, two, or three times a day. In an embodiment of the invention, a 14 g dose of the composition is administered to a human subject one, two, or three times a day. Thus, the total daily dosage given may be 1.5 g to 42 g for an average person of 70 kg weight and 5'7" height and may be used proportionally for larger or smaller persons based on weight or height.

Administering multiple doses of the amino acid composition per day may also be used as needed to provide the desired level of recovery of muscle strength and function. For instance, one, two, three, four, or more doses of the amino acid composition may be administered per day. In a preferred embodiment, one dose of the amino acid composition may be administered per day. In another preferred embodiment, two doses of the amino acid composition may be administered per day. In yet another preferred embodiment, three doses of the amino acid composition may be administered per day.

In some such methods the dose of methionine in either D or L configuration or a mixture thereof, or the hydroxyl analog thereof is at least 3 mg/kg/day but may be as high as 96 mg/kg/day.

The timing and duration of administration of the composition of the invention can vary. For instance, when the composition is administered to improve muscle strength and recovery from physical exercise, the composition may be administered before starting an exercise routine, during the exercise routine or after an exercise routine. Alternatively, when the composition is administered to improve muscle strength and recovery of a subject prone to muscle weakening such as an older human subject, the composition may be administered on a regular basis to maintain muscle strength and recovery. Or, when the composition is administered to improve muscle strength and recovery during rehabilitation from a post-traumatic injury, the composition may be administered throughout the post-traumatic rehabilitation period.

In some embodiments, when the composition is administered to improve muscle strength and recovery from physical exercise, the composition is administered before starting an exercise routine. In other embodiments, when the composition is administered to improve muscle strength and recovery from physical exercise, the composition is administered during the exercise routine. In yet other embodiments, when the composition is administered to improve muscle strength and recovery from physical exercise, the composition is administered after an exercise routine.

In an embodiment of the invention, the method of delivering is oral in liquid, solid or paste forms.

In other embodiments, wherein the taste of the composition may be improved without compromising efficacy, an artificial sweetener, such as aspartame, acesulfame K, sucralose, rebaudioside A (rebA), advantame, neotame, or Siraitia grosvenorii fruit extracts, may be added along with flavorings, such as cherry, grape, orange, mango, pineapple, lemon, vanilla, chocolate, peach, apple, etc.

In addition to the amino acid selection, the quantity of amino acids delivered in the compositions and methods disclosed herein also increases muscle strength, mass, and physical function. In a preferred embodiment, about 1.5 g of amino acids are delivered per serving with a daily intake of up to 42 g of amino acids.

In alternative or further embodiments, the composition may also comprise an excipient of supplemental minerals. Suitable minerals may include one or more minerals or mineral sources. Non-limiting examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

The compositions may also optionally comprise vitamins. The vitamins may be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

One or more low glycemic carbohydrates may be added to the formulations to provide the energy needed to produce the new protein without eliciting a significant insulin response. This energy source may also drive muscle growth more efficiently than food or other protein supplements in order to achieve muscle synthesis without causing users or patients to compensate for increased calorie intake. Such compounds, which may also be referred to as slow release saccharides, may include complex carbohydrates with long carbon chain lengths, including but not limited to nutriose, sucramalt, isomaltulose, dextrans, maltodextrin, and their functional equivalents. The elderly are generally resistant to the action of insulin, so avoiding an insulin response by using low glycemic carbohydrate will be advantageous to that population.

Low glycemic carbohydrate may comprise about 0-50% by mass. About two times the carbohydrate as total amino acids may be added, as this will provide the amount of energy needed for the stimulation of muscle protein synthesis resulting from the amino acids. In a preferred embodiment, up to 30 g of carbohydrate per serving may be added. These embodiments are based on the energy requirement of protein synthesis resulting from the amino acids, and the amount of energy supplied by the carbohydrate.

The composition may also comprise at least one excipient. Non-limiting examples of suitable excipients include a buffering agent, a preservative, a stabilizer, a binder, a compaction agent, a lubricant, a dispersion enhancer, a disintegration agent, a flavoring agent, a sweetener, a coloring agent, and combinations of any of these agents.

In an embodiment, the excipient is a buffering agent. Non-limiting examples of suitable buffering agents include sodium citrate, magnesium carbonate, magnesium bicarbonate, calcium carbonate, and calcium bicarbonate.

The excipient may comprise a preservative. Suitable examples of preservatives include antioxidants, such as alpha-tocopherol or ascorbate, and antimicrobials, such as parabens, chlorobutanol, or phenol.

In an alternative or further embodiment, the excipient may be a binder. Suitable binders include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In an alternative or further embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In yet another embodiment, the excipient may be a disintegrant. The disintegrant may be a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. The disintegrant may be an effervescent disintegrant. Suitable effervescent disintegrants include sodium bicarbonate in combination with citric acid, and sodium bicarbonate in combination with tartaric acid.

The excipient may include a flavoring agent. Flavoring agents may be incorporated into an outer layer and may be chosen from synthetic flavor oils and flavoring aromatics; natural oils; extracts from plants, leaves, flowers, and fruits; and combinations thereof. By way of non-limiting example, these may include cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia rebaudiana derivatives (Stevioside, rebaudioside A or C); chloro derivatives of sucrose such as sucralose; and sugar alcohols such as sorbitol, mannitol, xylitol, and the like.

Also contemplated as sweeteners are hydrogenated starch hydrolysates and 3,6-dihydro-6-methyl-1,2,3-oxathiazin-4-one-2,2-dioxide, particularly the potassium salt (acesulfame-K), and sodium and calcium salts thereof.

It may be desirable to provide a coloring agent. In another embodiment, the excipient may include suitable color additives, such as food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in certain embodiments.

The weight fraction of the excipient or combination of excipients in the formulation may be between 30% to 0.01% or less of the total weight of the amino acid composition.

Also contemplated are methods of delivery of the compositions disclosed herein, including but not limited to dosage. The compositions disclosed or made obvious herein may be formulated into a variety of forms and administered by a number of different means. The compositions may be administered orally, rectally, or parenterally, in formulations containing conventionally acceptable carriers, adjuvants, and vehicles as desired. The term "parenteral" as used herein includes subcutaneous, intravenous, intramuscular, or intrasternal injection, or infusion techniques. In an exemplary embodiment, the compounds of the invention are administered orally.

Solid dosage forms for oral administration may include capsules, tablets, caplets, pills, troches, chewables, lozenges, powders, and granules. A capsule typically comprises a core material comprising a composition of the invention and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

Alternatively, powders or granules embodying the compositions disclosed and made obvious herein may be incorporated into a food product. In a preferred embodiment, the food product may be a drink for oral administration. Non-limiting examples of a suitable drink include fruit juice, a fruit drink, an artificially flavored drink, an artificially sweetened drink, a carbonated beverage, a sports drink, a liquid diary product, a shake, and so forth to which excipients may also be added. Other suitable means for oral administration include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents. Additionally, chewable forms, as disclosed in U.S. Pat. No. 7,223,417, incorporated herein wholly by reference, may be used.

The beverage products disclosed here optionally contain a flavor composition, i.e., one or more flavor components, for example, natural or synthetic fruit flavors, botanical flavors, other flavors, and mixtures of any of them. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. The term berry also is used here to include aggregate fruits, i.e., not "true" berries, but those that are commonly accepted as a berry. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime and grapefruit, flavors such as apple, grape, cherry, and pineapple flavors and the like, and mixtures of any of them. In certain exemplary embodiments the beverage products comprise a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots and leaves. Also included within the term "botanical flavor" are synthetically prepared flavors made to simulate botanical flavors derived from natural sources. Examples of such flavors include cola flavors, tea flavors, and the like, and mixtures of any of them. The flavor component can further comprise a blend of the various above-mentioned flavors. In certain exemplary embodiments of the beverage products disclosed here, a cola flavor component or a tea flavor component is used. The particular amount of the flavor component useful for imparting flavor characteristics to the beverages of the present invention will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in at least certain exemplary embodiments of the beverage products disclosed here include, e.g., fruit, vegetable, and berry juices. Juices can be employed in the present invention in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices can be combined, optionally, along with other flavorings, to generate a beverage having a desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, tangerine, mandarin orange, tangelo, pomelo, grapefruit, yumberry, etc. Numerous additional and alternative juices suitable for use in at least certain exemplary embodiments will be apparent to those skilled in the art given the benefit of this disclosure. In the beverages of the present invention employing juice, juice may be used, for example, at a level of at least about 0.2% by weight of the beverage. In certain exemplary embodiments juice is employed at a level of from about 0.2% to about 40% by weight of the beverage.

Organic acids compatible with the components may be employed in an embodiment. Such acids include citric acid, malic acid and other food compatible acids.

Certain such juices which are lighter in color can be included in the formulation of certain exemplary embodiments to adjust the flavor and/or increase the juice content of the beverage without darkening the beverage color. Examples of such juices include apple, pear, pineapple, peach, lemon, lime, orange, apricot, grapefruit, tangerine, rhubarb, cassis, quince, passion fruit, papaya, mango, guava, litchi, kiwi, mandarin, coconut, and banana. Deflavored and decolored juices can be employed if desired.

The compositions may also be a solid foodstuff. Suitable examples of a solid foodstuff include a food bar, a snack bar, a cookie, a brownie, a muffin, a cracker, a chewable gum, an ice cream bar, a frozen yogurt bar, a chewy snack and the like. In an embodiment, the method comprises administering the composition as described above multiple times per day, or if taken as a liquid, may be mixed and taken throughout the day.

In an alternative or further embodiment of a method of delivery, the composition may also be used in conjunction with exercise. For example, the composition may be given before, during or immediately after exercise. In such embodiments, the composition may be in the form of a sports drink.

Without further elaboration, it is believed that one of ordinary skill in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise specified, parts and percentages are by weight.

EXAMPLES

Formulations

Formulations useful in the invention comprise the nine essential amino acids, with the content of certain components being elevated and/or optimized. Additional semi-essential amino acids, additional amino acids and other components may be added to optimize the formulation in accordance with the guidelines above.

By following the guidelines above, formulations in powder, liquid suspension (e.g., for preparation and administration in drink form), chewable "bite" form, food bar form and/or capsule form may be prepared, in accordance with the proportions, as follows:

Example 1

| Formula 1* | | |
|---|---|---|
| EAA | mg/serving** | |
| Histidine | 280 | 8.0% |
| Isoleucine | 360 | 10.2% |
| Leucine | 560 | 15.9% |
| Lysine | 410 | 11.6% |
| Methionine | 560 | 15.9% |
| phenylalanine | 560 | 15.9% |
| Threonine | 250 | 7.1% |
| Tryptophan | 130 | 3.7% |
| Valine | 410 | 11.6% |
| Arginine | | |
| Total | 3520 | |

*Note: Each of the Formulations listed herein may be associated with a given utility/utilities or method/methods of treatment (e.g., increasing strength in elderly). However, as will be readily apparent to those skilled in the art after reading the present specification, each of the Formulations is useful in each of the aspects discussed herein.
**Note: Similar conversions of percentages to mg/serving as shown in this Table, may be made based on similar data and information throughout this disclosure.

Example 2

| Formula 2 | | |
|---|---|---|
| | mg/serving | |
| Histidine | 280 | 4.3% |
| Isoleucine | 360 | 5.6% |
| Leucine | 560 | 8.7% |
| Lysine | 410 | 6.3% |
| Methionine | 560 | 8.7% |
| phenylalanine | 560 | 8.7% |
| Threonine | 250 | 3.9% |
| Tryptophan | 130 | 2.0% |
| Valine | 410 | 6.3% |
| Arginine | 2940 | 45.5% |
| | 6460 | 100.0% |

Example 3

| Formula 3 | | |
|---|---|---|
| | mg/serving | |
| L-histidine | 280 | 5.2% |
| L-isoleucine | 360 | 6.6% |
| L-leucine | 560 | 10.3% |
| L-lysine | 410 | 7.6% |
| L-methionine | 560 | 10.3% |
| L-phenylalanine | 560 | 10.3% |
| L-threonine | 250 | 4.6% |

-continued

| Formula 3 | | |
|---|---|---|
| | mg/serving | |
| L-tryptophan | 130 | 2.4% |
| L-valine | 410 | 7.6% |
| L-arginine | 1910 | 35.2% |
| Total | 5430 | 100.0% |

Example 4

| Formula 4 | | |
|---|---|---|
| amino acid | mg/serving | |
| histidine | 280 | 5.1% |
| isoleucine | 360 | 6.5% |
| leucine | 2040 | 37.0% |
| lysine | 410 | 7.4% |
| methionine | 560 | 10.1% |
| phenylalanine | 560 | 10.1% |
| threonine | 250 | 4.5% |
| tryptophan | 130 | 2.4% |
| valine | 410 | 7.4% |
| arg | 520 | 9.4% |
| | 5520 | |

Example 5

| Formula 5 | | |
|---|---|---|
| | mg/serving | |
| histidine | 280 | 4.1% |
| isoleucine | 360 | 5.2% |
| leucine | 2040 | 29.5% |
| lysine | 410 | 5.9% |
| methionine | 560 | 8.1% |
| phenylalanine | 560 | 8.1% |
| threonine | 250 | 3.6% |
| tryptophan | 130 | 1.9% |
| valine | 410 | 5.9% |
| arginine | 1910 | 27.6% |
| | 6910 | 100.0% |

Administration/Dosage/Supplementation

In general, the foregoing content guidelines may be followed to provide administration in the form of a serving, including daily servings and multiple servings per day. Such servings may be in any of the suitable forms of oral administration discussed above, including the solid forms and in, for example, suspension form, such as a drink or smoothie or similar preparation. Commercial drink preparations made from vegetables, fruits serve well as carriers in which the amino acids dissolved or dispersed and then be ingested. Sports drinks and bottled waters also serve well as carriers in which the amino acids can be dissolved or dispersed and then be ingested. Milk, flavored milks, imitation milks, such as soy, rice and almond milks serve well as carriers in which the amino acids can be dissolved or dispersed and then be ingested. Juices, either homemade or commercially prepared can be used as carriers in which the amino acids can be dissolved or dispersed and then be ingested. The amino acids can be dissolved or dispersed in sodas and then be ingested. Gels or puddings may be used to incorporate the amino acids prior to ingestion.

Example 7

Two subjects, a 74 year old male and an 86 year old female, both of whom were declining in their ability to walk and to stand up were placed on a regimen of 6.7 g/day of a formula of amino acids containing L-histidine, 4.3%; L-isoleucine, 5.6%; L-leucine, 8.7%; L-lysine, 6.3%; L-methionine, 8.7%; L-phenylalanine, 8.7%; L-threonine, 3.9%; L-tryptophan, 2.0%; L-valine, 6.3%; and L-arginine, 45.5%, taken in either orange juice or cranberry juice. After four weeks the distance walked was increased by 300% and the time to stand was reduced by 80%.

Example 8

An 86 year old male, who had not walked other than around his house and who had not played the piano in 2 years began taking, without any other changes in his routine, 3 servings in orange juice daily, 3.5 g each, of a formula of amino acids containing L-histidine, 8%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%. Two days later, he spontaneously played the piano, something he had not done for the previous 2 years. Seven days after beginning drinking the formulation he began walking around the block. Two weeks later, he was walking ½ mile each day.

Example 9

A 73 year old male began a mountain bike routine of approximately 5 miles with an elevation gain of 360 feet. During each ride, the subject took one serving of 11 g, in a commercially available sports drink containing, minerals, sugars, artificial sweeteners and flavors, diluted with water, of a formula of amino acids containing L-histidine, 3.7%; L-isoleucine, 4.8%; L-leucine, 27.1%; L-lysine, 5.5%; L-methionine, 7.4%; L-phenylalanine, 7.4%; L-threonine, 3.3%; L-tryptophan, 1.7%; L-valine, 5.5%; and L-arginine, 33.5%; during the ride and one serving of 11 g within 30 minutes after the ride. Rides were made 1-3 times per week for 1 month. The time required per ride decreased by 23% during this period. Although thoroughly fatigued at the end of the ride, the fatigue was relieved 15 minutes after consumption of the second serving. The biker also noted no soreness occurred the day after the rides if an additional serving of the composition was taken at the end of the ride.

Example 10

A common condition on the ski slopes is being extremely tired and sore after one or more days of skiing. Skiing when stiff and sore may lead to injury when unable to react to uneven conditions.

A 63 year old who was ready to stop skiing about 1 hour after lunch, due to fatigue, drank one serving of 11 g, of a drink containing minerals, sugars, artificial sweeteners and flavors and a formula of amino acids consisting of L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6%; and L-arginine, 35.2% at the beginning of a 12 minute lift ride. After a 25 minute descent, the fatigue had stopped and the skier was able to ski 2 more runs over the next hour prior to being in the fatigued condition he experienced before drinking the amino acid formula. This was repeated the next 3 days with the skier extending his skiing time by 1-2 hours each day.

Example 11

Three skiers, 29, 41 and 63 years of age drank one serving of 11 g of the formulation in Example 10 in the evening after skiing a full day on the slopes and noticed the next morning that they were not sore. This was repeated each day over a three day period and all experienced greatly decreased muscle soreness and fatigue each morning.

Example 12

A 28 year old skier drank one serving of 11 g, in a drink containing minerals, sugars, artificial sweeteners and flavors and a formula of amino acids consisting of L-histidine, 3.3%; L-isoleucine, 4.2%; L-leucine, 6.6%; L-lysine, 4.8%; L-methionine, 6.6%; L-phenylalanine, 6.6%; L-threonine, 2.9%; L-tryptophan, 1.5%; L-valine, 4.8%; and L-arginine, 58.7%; and experienced a significant increase in energy, allowing him to continue skiing on the slopes 2 hours past his stopping time the previous day. This was repeated on the following 3 days with the same extension of skiing time.

Example 13

A 38 year old woman who irregularly ran 5K's with her coworkers started taking one serving after each run of 3.5 g of amino acids in a formula containing L-histidine, 8%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%, along with flavorings and sweeteners for taste. She reported that the morning following her runs which included the essential amino acid formula she experienced none of the soreness she had previously experienced after such intermittent runs, while her coworkers all complained of soreness Example 14

A 73 year old male, 6'1", 195 lbs., underwent surgery for total knee replacement. Starting 1 week before and continuing for 6 weeks after surgery, the subject took 2 servings daily of 6.5 g each, of a drink containing minerals, sugars, artificial sweeteners, fruit or vegetable juice, and flavors with a formula of amino acids containing L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6%; and L-arginine, 35.2%. Recovery from surgery was 25% quicker than the surgeon's expected value.

Scarring of the knee after replacement surgery was described as much lower than she had seen upon examination at 6 weeks post-surgery by an x-ray technician with 5 years of experience examining the surgical results of the surgeon who performed the surgery, resulting in her inquiry concerning the creams the patient might have used to obtain such results. Only inexpensive over the counter moisture creams had been used.

A physical therapist with 8 years of dealing with total knee replacements examined the scar and estimated healing to be superior to any other of her cases at 4 days post-surgery. After removal of staples at 14 days, the scar appearance was still superior to all other cases she had seen. Progress on strength recovery after surgery was estimated to be in the top 1% of patients in the physical therapist's experience.

At 9 weeks post-surgery, the 7" scar on the patient's knee was less than 2 mm wide, no traces of stapling remained, the scar was not different in appearance from surrounding skin for 3" and had only a slight redness for the remainder. At 13 weeks, only 1" of the scar was visibly different from the surrounding area. A surgical scar on the same knee, which was 46 years older, was 3-5 mm wide and clearly visible as a white streak.

During the 8 week recovery period of the total knee replacement, the patient noticed extreme fatigue after limited amounts of exercise in physical therapy. He found that upon drinking 2 servings of the above formula, his energy was restored in 15-25 minutes.

At 8 weeks post-surgery, the patient resumed mountain biking. He took 2 servings of the above composition during a ride lasting 54 minutes and covering a distance 3.35 miles, with a 92 ft rise and fall in elevation, in which his heart rate ranged from 82 to 155, averaging 135 bpm, with only minor fatigue throughout the ride. He took another 2 servings at the completion of the bike ride and restored his energy level to normal.

During a speaking engagement 9 weeks post-surgery, the patient noticed significant fatigue on standing and speaking for a 50 minute lecture. He took 2 servings of the above amino acid composition in a drink and recovered in 25 minutes to a normal fatigue level. He then gave another 45 minute lecture while standing without fatigue.

Example 15

A 65 year old woman with advanced colon cancer was given 3 servings daily, 3.5 g each, of a formula of amino acids containing L-histidine, 8%; L-isoleucine, 10.2%; L-leucine, 15.9%; L-lysine, 11.6%; L-methionine, 15.9%; L-phenylalanine, 15.9%; L-threonine, 7.1%; L-tryptophan, 3.7%; and L-valine, 11.6%. The formula, including flavorings and sweeteners for taste, was placed in a milkshake, made with ice cream of the patient's choosing, due to her frequent vomiting and reluctance to eat most foods, to be drunk through the course of the day as the patient desired. Although this occurred in the last two weeks of her life, her caretaker noted the patient began to gain weight and had more strength to stand and walk.

Example 16

A 37 year old woman underwent bariatric surgery and found that as she lost weight, she could not maintain her muscle mass on the restricted volume of food. She began taking 3 servings daily in a fruit smoothie often containing yogurt, of 3.5 g of a formula of amino acids containing L-histidine, 3.3%; L-isoleucine, 4.2%; L-leucine, 6.6%; L-lysine, 4.8%; L-methionine, 6.6%; L-phenylalanine, 6.6%; L-threonine, 2.9%; L-tryptophan, 1.5%; L-valine, 4.8%; and L-arginine, 58.7%. She found she could maintain muscle mass while losing 100 lbs.

Example 17

A 34 year old male underwent arthroscopic knee surgery for anterior cruciate ligament repair. Starting 1 week before and continuing for 6 weeks after surgery, the subject took 2-4 servings daily of 6 g each, of a formula of amino acids containing L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6% and L-arginine, 35.2%. Recovery from surgery was 25% quicker than the surgeon's expected value.

A 68 year old male underwent surgery for rotator cuff repair. Starting 1 week before and continuing for 6 weeks after surgery, the subject took 3 servings daily of 6 g each, of a formula of amino acids containing L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6% and L-arginine, 35.2%. Recovery from surgery was 25% quicker than the surgeon's normally expected value.

Example 18

A 38 year old woman, 5'5", with Stage 3 Breast Cancer underwent bilateral mastectomy followed two months later by chemotherapy with taxotere and cytoxan in 6 rounds over 4' months while taking 1 serving daily, 11 g, of a formula of amino acids containing L-histidine, 4.7%, L-isoleucine, 6.0%, L-leucine, 9.3%, L-lysine, 6.8%, L-methionine, 9.3%, L-phenylalanine, 9.3%, L-threonine, 4.2%, L-tryptophan, 2.2%, L-valine, 6.8% and L-arginine, 41.5%. She was frequently unable to eat most foods during her chemotherapy, but was able to take the amino acid formula in a taste masked formula containing sweeteners and flavorings, as a drink, mixed with various kinds of fruit and vegetable juices. A physical therapist specializing in oncology rehabilitation noted that she healed much quicker than her other patients and that the scarring after her surgery was remarkably low. After switching to another physical therapist after chemotherapy and following surgery for implants, the therapist asked where her scars were. Upon learning that she would have to undergo DIEP flap reconstruction surgery 1.5 years after her mastectomy, she began taking the above amino acid formula 2½ months prior to the surgery. The surgeon noted unusually well-developed abdominal muscle mass for a woman of her age and previous treatment regimen. The DIEP flap reconstruction surgery showed minimal scarring and the healing was reported by her surgeon to be more rapid than normal.

She noted that persons often mistake her for her daughter due to the noticeable lack of fine lines and wrinkles around her eyes and forehead. Her skin tone overall is firm and elastic.

Example 19

A 67 year old woman began an essential amino acid formula in water with Crystal Light™ containing the following concentrations of amino acids in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6% and L-arginine, 35.2% for increasing her strength. After a few months, she noticed her skin was no longer getting thinner. At 69, she was diagnosed with breast cancer and both her surgeon and the surgeon's physician assistant noted the exceptional quality of the skin on her neck, chest and breasts. She began radiation therapy and again, the oncologist and her nurse commented on the quality of her skin. At each weekly checkup, it was noted that there was no deterioration of her skin quality caused by radiation.

In addition to the specific results observed in the foregoing examples, the results confirm that the treated condition was markedly improved in comparison with a subject or subjects who were not administered compositions of the invention.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The invention claimed is:

1. A nutritional composition comprising:
    an amino acid component, said amino acid component comprising by weight of total essential amino acids:
    3-9% of L-histidine;
    4-11% of L-isoleucine;
    3-37% of L-leucine;
    4-12% of L-lysine;
    6-17% of L-phenylalanine;
    0.3-9% of L-threonine;
    1-4% of L-tryptophan;
    4-19% of L-valine;
    27.6-60% of L-arginine;
    10.3-17% of L-methionine; and
    wherein the nutritional composition optionally comprises an artificial sweetener and, optionally, a flavoring component.

2. The composition of claim 1, in the form of a single serving wherein L-methionine is present in an amount of at least 400 mg methionine per 10 g of said component administered.

3. The composition of claim 1, further comprising an additional amino acid selected from the group consisting of L-citrulline, L-cysteine, L-carnitine, creatine and mixtures thereof.

4. The composition of claim 1, wherein L-arginine is present in an amount of 35.2-60%.

5. The composition of claim 4, wherein L-arginine is present in an amount of 35.2% to 45.5%.

6. A method for treating one or more of: muscle mass, strength, functional performance, fatigue, soreness and recovery from disease treatment or surgery in a human subject, comprising:
    administering to a subject in need of such treatment a composition comprising an amino acid component, said amino acid component comprising by weight of total essential amino acids:
    3-9% of L-histidine;
    4-11% of L-isoleucine;
    3-37% of L-leucine;
    4-12% of L-lysine;
    6-17% of L-phenylalanine;
    0.3-9% of L-threonine;
    1-4% of L-tryptophan;
    4-19% of L-valine;
    27.6-60% of L-arginine;
    10.3-17% of L-methionine; and
    wherein the composition optionally comprises an artificial sweetener and, optionally, a flavoring component.

7. The method of claim 6, wherein the amino acid component comprises the following concentrations of amino acids in terms of w/w %: L-histidine, 3-9%; L-isoleucine, 4-11%; L-leucine, 8.7-15.9%; L-lysine, 6.3-12%; L-methionine, 10.3-17%; L-phenylalanine, 6-17%; L-threonine, 0.3-9%; L-tryptophan, 1-4%; L-valine, 4-19%; and L-arginine, 35.2-60%.

8. The method of claim 6, wherein the amino acid component comprises, in terms of w/w %: L-histidine, 3-9%; L-isoleucine, 4-11%; L-leucine, 8.7-15.9%; L-lysine, 6.3-11.6%; L-methionine, 10.3-17%; L-phenylalanine, 8.1-15.9; L-threonine, 0.3-9%; L-tryptophan, 1-4%; L-valine, 4-11.6%; and L-arginine, 35.2-45.5%.

9. The method of claim 6, wherein the amino acid component comprises, in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6%; and L-arginine, 35.2%.

10. A method for improving one or more of wound healing, wound outcomes, and surgical recovery in a human subject comprising:
    administering to a subject in need of such treatment a composition comprising an amino acid component, said amino acid component comprising by weight of total essential amino acids:
    3-9% of L-histidine;
    4-11% of L-isoleucine;
    3-37% of L-leucine;
    4-12% of L-lysine;
    6-17% of L-phenylalanine;
    0.3-9% of L-threonine;
    1-4% of L-tryptophan;
    4-19% of L-valine;
    27.6-60% of L-arginine;
    10.3-17% by weight of L-methionine; and
    wherein the composition optionally comprises an artificial sweetener and, optionally, a flavoring component.

11. The method of claim 10, wherein the amino acid component comprises the following concentrations of amino acids in terms of w/w %: L-histidine, 3-9%; L-isoleucine, 4-11%; L-leucine, 8.7-15.9%; L-lysine, 6.3-12%; L-methionine, 10.3-17%; L-phenylalanine, 6-17%; L-threonine, 0.3-9%; L-tryptophan, 1-4%; L-valine, 4-19%; and L-arginine, 35.2-60%.

12. The method of claim 10, wherein the amino acid component comprises, in terms of w/w %: L-histidine, 3-9%; L-isoleucine, 4-11%; L-leucine, 8.7-15.9%; L-lysine, 6.3-11.6%; L-methionine, 10.3-17%; L-phenylalanine, 8.1-15.9; L-threonine, 0.3-9%; L-tryptophan, 1-4%; L-valine, 4-11.6%; and L-arginine, 35.2-45.5%.

13. The method of claim 10, wherein the amino acid component comprises, in terms of w/w %: L-histidine, 5.2%; L-isoleucine, 6.6%; L-leucine, 10.3%; L-lysine, 7.6%; L-methionine, 10.3%; L-phenylalanine, 10.3%; L-threonine, 4.6%; L-tryptophan, 2.4%; L-valine, 7.6%; and L-arginine, 35.2%.

14. The method of claim 6, wherein a dose of 1.5 g to 42 g of the said amino acid component is administered one, two, or three times a day or such doses are administered over a 24 hour period.

15. The method of claim 10, wherein a dose of 1.5 g to 42 g of the said amino acid component is administered one, two, or three times a day or such doses are administered over a 24 hour period.

16. The method of claim 6, wherein the administration is oral.

17. The method of claim 10, wherein the administration is oral.

18. The composition of claim 1, further comprising an artificial sweetener and, optionally, a flavoring component.

19. The composition of claim 18, wherein the artificial sweetener is aspartame, acesulfame K, sucralose, rebaudioside A (rebA), advantame, neotame, or Siraitia grosvenorii fruit extracts.

20. The method of claim 6, wherein the composition further comprises an artificial sweetener and, optionally, a flavoring component.

21. The method of claim 20, wherein the artificial sweetener is aspartame, acesulfame K, sucralose, rebaudioside A (rebA), advantame, neotame, or Siraitia grosvenorii fruit extracts.

22. The method of claim 10, wherein the composition further comprises an artificial sweetener and, optionally, a flavoring component.

23. The method of claim 22, wherein the artificial sweetener is aspartame, acesulfame K, sucralose, rebaudioside A (rebA), advantame, neotame, or Siraitia grosvenorii fruit extracts.

* * * * *

UNITED STATES PATENT AND TRADEMARK OFFICE
CERTIFICATE OF CORRECTION

| | | |
|---|---|---|
| PATENT NO. | : 11,285,124 B2 | |
| APPLICATION NO. | : 16/639233 | |
| DATED | : March 29, 2022 | |
| INVENTOR(S) | : G. Calton | |

It is certified that error appears in the above-identified patent and that said Letters Patent is hereby corrected as shown below:

In the Claims

Column 36, Line 16 (Claim 8, Line 5) please change "15.9;" to -- 15.9%; --
Column 36, Line 56 (Claim 12, Line 5) please change "15.9;" to -- 15.9%; --

Signed and Sealed this
Twenty-seventh Day of September, 2022

Katherine Kelly Vidal
Director of the United States Patent and Trademark Office